United States Patent

Löfstedt

[11] Patent Number: 5,116,311
[45] Date of Patent: May 26, 1992

[54] METHOD FOR DRUG ADMINISTRATION

[76] Inventor: Sigmund J. Löfstedt, St. Pauligatan 22, Jönköping, Sweden, S-552 58

[21] Appl. No.: 602,393

[22] Filed: Oct. 25, 1990

Related U.S. Application Data

[63] Continuation of Ser. No. 275,120, Nov. 22, 1988, abandoned.

[30] Foreign Application Priority Data

Nov. 30, 1987 [SE] Sweden .............................. 8704767

[51] Int. Cl.⁵ .................... A61M 31/00; A61M 11/00
[52] U.S. Cl. ................................. 604/54; 128/200.22
[58] Field of Search .............. 604/49, 54, 93, 94, 604/131, 246, 257; 128/898, 200.14, 200.22, 200.21

[56] References Cited

U.S. PATENT DOCUMENTS

| 716,931 | 12/1902 | Pattison | 604/19 |
| 1,502,163 | 7/1924 | Sprague | 604/94 |
| 2,078,180 | 4/1937 | Kronenberg | 604/94 |
| 2,883,983 | 4/1959 | Biederman | 604/94 |
| 3,066,669 | 12/1962 | DeMelfy | 604/94 |
| 3,211,149 | 10/1965 | Fono | 604/77 |
| 3,847,145 | 11/1974 | Grossan | 128/66 |

Primary Examiner—Randall L. Green
Assistant Examiner—R. Clarke
Attorney, Agent, or Firm—White & Case

[57] ABSTRACT

A new method for administration of pharmacological solutions into the nasal cavity whereby the patient's head is being bent forward 55°-90° from an upright position as well as a device for use in the administration. The method makes it possible to irrigate or treat the whole or nearly the whole mucous membrane in the nasal cavity with solutions or suspensions without any risk for their reaching the digestive tract through the pharynx.

8 Claims, 2 Drawing Sheets

METHOD FOR DRUG ADMINISTRATION

This application is a continuation of application Ser. No. 275.120. filed on Nov. 22, 1988 abandoned.

FIELD OF THE INVENTION

The present invention is directed to a new method for the administration of drugs into the nasal cavities as well as the use of the method for the irrigation of the nasal mucosa and a new device for systemic administration of drugs in solutions via the nasal mucous membranes.

BACKGROUND OF THE INVENTION

Administration of decongestant nose drops in the form of spray or drops to the nose rapidly decongests parts of the mucous membrane in the nasal cavity and makes breathing through the nose easier. Distribution studies show, however, that the nose drops do not reach the whole mucous membrane surface in the nose. With the traditional administration forms of nose drops, there are difficulties to reach, among other parts of the nose, the osties under the turbinates. It is desirable to be able to reach these parts at the treatment of illnesses, e.g. sinusitis, which cannot be cured by current local treatment.

Another way of administering solutions into the nasal cavities is by allowing a solution flow through a tightening olive, which fits to the nostril, on its upper side and can be attached to some kind of container or tube on its bottom. Although the olive fits the nostril, it is not possible to fill the nose and let the solution reach the upper and inner parts of the nose, as the solution runs back into the pharynx along the bottom of the cavities.

When there has been a need to irrigate the nasal cavities, because of mucous dryness or soreness, a transparent pear shaped container, "Nasal-Duck", holding about 90 ml of solution has been used. The container has a "neck" at one end and the top of said neck is inserted into the nostril at use. At use the container is half-filled with an isotonic solution containing sodium chloride and sodium hydrogen carbonate having a pH of 7.6. The patient regulates the flow of the solution by applying his index finger against a refilling hole on the upper side of the container. The described container, however, has some drawbacks as the solution easily flows back into the pharynx, and thus cannot reach the whole nasal mucous membrane.

From U.S. Pat. No. 3,847,145 a nasal irrigation system is known, which uses a pulsating flow of isotonic sodium chloride in order to irrigate the nasal system. The solution leaves the nasal system either via one nostril or the mouth. The described device is only used in order to irrigate the nasal system not to administer drugs.

It has thus been a need for the development of a method and a device, which makes it possible to fill one nasal cavity almost completely with drug solution, thereby reaching the osties and covering the whole nasal mucous membrane surface while avoiding the solution to run back into the pharynx.

BRIEF DESCRIPTION OF DRAWINGS

According to the present invention a new technique has been developed, where one half of the nasal cavity can be filled at a time and bringing a drug into contact with the whole nasal mucous membrane with the exception of a small part, namely the ostia of the rear ethmoidal cells and the sphenoidal sinus without any risk of the solution running back into the pharynx, which is undesirable. By keeping the solution in motion, nearly the whole nasal mucous membrane is effectively irrigated. When the solution contains a drug, the drug concentration and the time of exposure are the factors which decide the degree of the local effect on the mucosa membrane, as well as possible systemic absorption of the drug. The new technique can also be used in order to offer a better technique for nasal lavage and cleaning of the nasal cavity.

The new technique is described in detail in the following:

The person, sitting or standing, who shall have the nasal administration bends his head forward approximately 60° or more from an upright position. Preferably the head is bent between 55°–90°. The "threshold" between the nasal cavity and the pharynx is then on a higher level than the inner end of the septum. When a solution is administered through a tightening olive shaped "balloon" from a container provided with a tube and an airing pipe, alternatively from an enema can, an ear syringe or from a compressible container for example formed as a bellows syringe with a tightening olive shaped "balloon", one half of the nasal cavity will be filled, except for a smaller part above the upper nasal turbinate. When the head is bent forward 90° also the parts above the upper nasal turbinate are covered. Excessive filling will cause the overflow to run out through the other nostril and not back into the pharynx with no distress for the patient. The solution can be kept in motion by rising and lowering the container repeatedly, respectively by pressing together/releasing the compressible container. When the treatment is completed, the solution may run back into the container.

Figure 1:
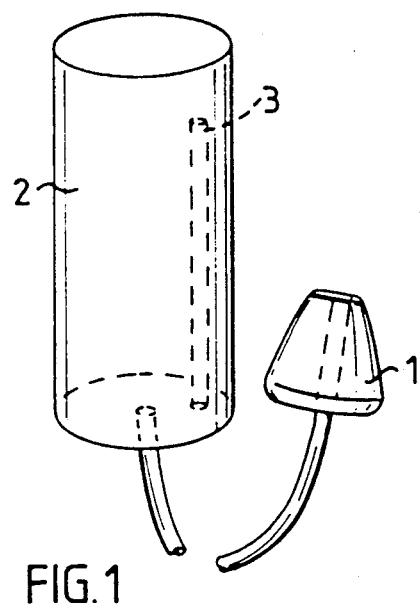

The invention is described with reference to the following figures:

FIG. 1 shows a view from the sides of one device according to the invention.

Figure 2:
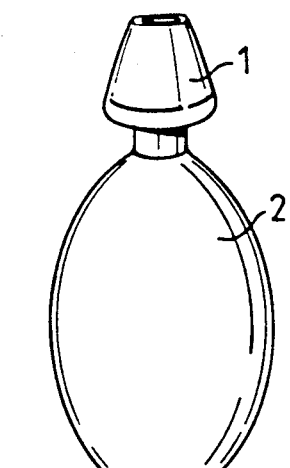

FIG. 2 shows a view from the side of a preferable device according to the invention.

Figure 3:
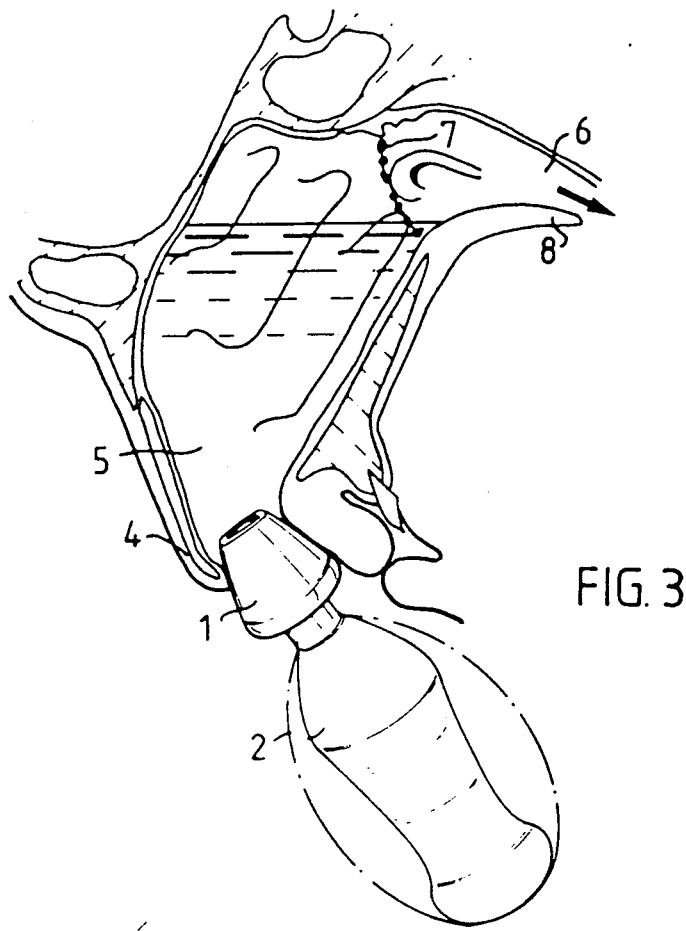

FIG. 3 illustrates a sectional view of the nasal cavities, when the patient bends his head 60° from an upright position.

Figure 4:
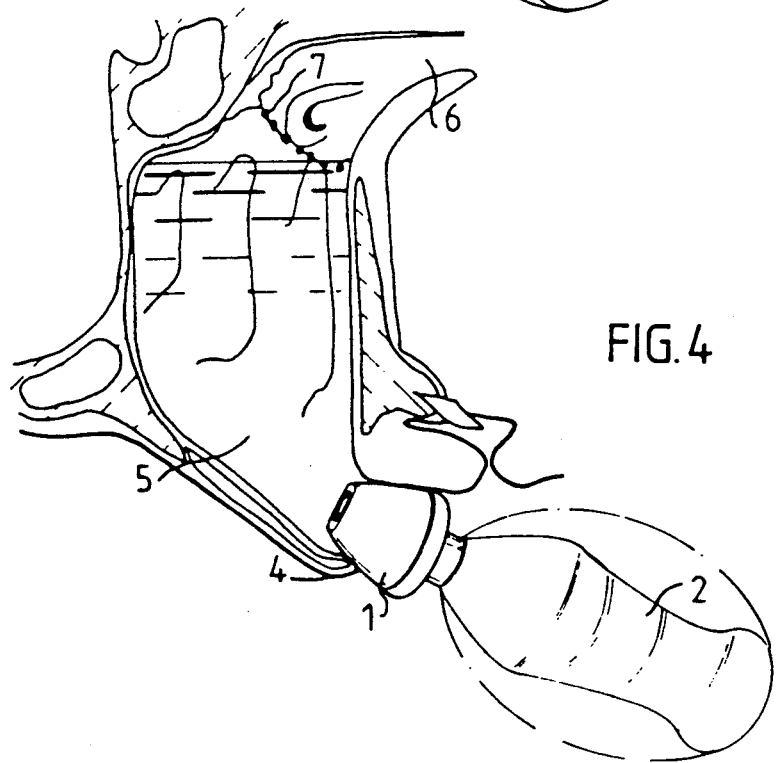

FIG. 4 illustrates a sectional view of the nasal cavities, when the patient bends his head 90° from an upright position.

For the new technique of administration it is necessary to use a device which fits to the nostril at one end (1) and at the other end consists of a container (2), preferably prefilled with the solution that is to be administered. It is especially preferred to form the container as a compressible container, e.g. a bellows shaped container as in that case no airing pipe is necessary as the nasal cavity can be filled and the solution held in motion by compressing and releasing the container. If the container is made rigid it is necessary to have an airing pipe (3). The rigid container is illustrated in FIG. 1. Furthermore the rigid container must be rised and lowered in order to keep the solution in motion within the nasal cavity.

It is important that the upper opening part, preferably in the form of an olive has an opening, which is not too small, preferably the diameter is between 3–10 mm. It is especially preferable that the diameter of the opening of the container is 7 mm. If the opening is too small the pressure inside the container may cause the content to be sprayed or jet streamed into the nasal cavity. This must be avoided, as there in this case is a risk that the solution can run back into the pharynx and not cover the whole membrane. In order to get a proper tightening of all sizes of nostrils the olive must be conical and the diameter of the base is 15-23 mm, preferably 19 mm.

The preferable device according to the invention is described in detail in the following with reference to FIG. 2. The upper part of the device, which fits the nostril, namely the olive (1), is conical. The lower part is a container (2) made in a compressible material, preferably plastic. The device is prefilled with the solution to be administered.

FIG. 3 illustrates a side view of the nasal cavity filled with a solution, when the head is bent forward 60° from an upright position. The container (2) with the olive (1) fits into the nostril (4). The nasal cavity is filled with solution (5). As can be seen the level of the solution is not reaching the uppermost parts of the nasal cavity and no solution runs down the pharynx (6). The lowest opening (7) between the nasal cavities is lower than the threshold (8) between the nasal cavity and the pharynx.

FIG. 4 illustrates a side view of the nasal cavity filled with a solution (5), when the head is bent forward 90° from an upright position. Also the openings (7) between the nasal cavities can be seen. The container (2) with the olive (1) fits into the nostril (4). With the higher degree of bending also the osties of the rear ethmoidal cells and the sphenoidal sinus are covered by the solution.

Tests with bellows containers filled with physiological salt solution show that the volume which can be filled in one of the nasal cavity with the described technique varies from one half of the nasal cavity to the other half and from person to person. Repeated tests in the same nasal cavity show only minor variations in volume with this technique.

Tests have also been cried out in order to find the optimal way to tilt the head. It was found that some of the test persons only needed to bend their heads 15° from an upright position when others needed to bend it as much as 53° in order to avoid the solution from running into the pharynx. Thus 60° from an upright position gives a margin, which makes the method usable on all persons. Thus the method and the device can be used to measure the volume of the nasal cavities, as well as changes in the volume. Swelling of the mucous membrane encroches on the air space on provocation with allergens for diagnostic purposes. In order to establish the swelling or decongestant effect of drugs, for example α-agonists, the space is measured before and after exposure and the change is calculated.

PHARMACOLOGICAL EXAMPLES

The effect on the equivalent ostial diameter was studied after application of traditional nose drops Nezeril 0.5 mg/ml, 0.1 ml, metered as spray and corresponding placebo as well as after diluted Nezeril 0.1 mg/ml and corresponding placebo administered by the technique with bellows containers according to the invention with the head bent forward 60°. Nezeril contains as the active ingredient oxymetazoline chloride.

The ostial diameter was measured with the following technique:

A pressure-flow technique developed by Aust & Drettner in 1974 and modified by Ivarsson et al in 1983, 1984 (cf Ivarsson A et al: Patency tests of the maxillary ostium - model experiments. Acta Otolaryngol 1983;96:294-305 and Jannert M et al: Patency of the maxillary sinus ostium in healthy individuals. Acta Otolaryngol 1984;97:137-149) was used to measure the ostial airway resistance from which the corresponding ostial diameter can be calculated. A special cannula was used to record the pressure rise within the sinus, at an artificial air-flow directed from the sinus, into the nasal cavity. Ostial diameter was calculated in both the sitting and the recumbent position.

The study was designed as a randomized cross-over open study with single dose administration. Five healthy volunteers were allocated at random to one of two treatments in two phases separated by at least two days wash-out.

Treatment 1: Placebo spray followed after 50 minutes by oxymetazoline chloride 0.5 mg/ml spray (0.1 ml).

Treatment 2: Placebo solution (with bellows container) followed after 50 minutes by oxymetazoline chloride 0.1 mg/ml solution. 10-18 ml was administered with a special bellows container during 30 seconds into the nose.

Equivalent ostial diameter was recorded before the start and during the whole experiment.

The dosage of oxymetazoline was 1) two puffs of Nezeril 0.5 mg/ml in one nostril = 0.1 ml.

2) oxymetazoline 0.1 mg/ml—about 10-18 ml, time of exposure 30 seconds.

Placebo and Nezeril were supplied immediately after the completed measuring in a recumbent position at 5 and 50 minutes respectively. Of Nezeril 0.5 mg/ml or alternatively placebo spray 2 puffs = 0.1 ml were given. The container for the new way of administration was filled with 25 ml Nezeril 0.1 mg/ml or alternatively placebo. Of this 10-18 ml was estimated to reach the nasal cavity, which was exposed during 30 seconds (the overflow ran out from the other nostril). After the time of exposure the solution ran back into the container.

After the end of the test statistical comparisons were made between the effects on the equivalent ostial diameter of Nezeril (oxymetazoline) and corresponding placebo with the two administration forms.

No side effects of any kind were seen during this experimental study.

Results

Paired comparisons with t-test show that Nezeril 0.1 mg/ml given with bellows container resulted in significant (p 0.05) greater ostial diameter compared with corresponding placebo. Nezeril spray 0.5 mg/ml showed no effect on the maxillary ostial diameter in comparison with the effect of corresponding placebo, cf Table 1.

TABLE 1

| Equivalent ostial diameters and results of t-tests of the differences. (n = 5) | | | | | | |
|---|---|---|---|---|---|---|
| | Nezeril | | Placebo | | Difference Nezeril-Placebo | |
| | mean | SD | mean | SD | mean | SD | significance |
| Spray | 1.80 | 1.11 | 1.71 | 0.90 | 0.09 | 0.26 | N.S |
| Bellow | 2.05 | 0.54 | 1.11 | 1.03 | 0.95 | 0.59 | p < 0.05 |

Discussion

After treatment with Nezeril 0.1 mg/ml with bellows container during 30 seconds there was a significant decongestant effect during the whole observation time of 50 minutes on the mucous membrane in the maxillary sinus ostium. With the placebos and the Nezeril spray 0.5 mg/ml there were no such effects. The results indicate that the administration method with a decongestant solution filling one of the nasal cavities from a bellows container while the head is bent forward approximately 60° from the upright position is an effective treatment from. It is obvious that the decongestant solution has reached at least the entrance of the ostial channel.

The results indicate that Nezeril solution given with bellows container in the manner described above, will give a decongestant effect on the osties. With the new technique of filling one half of the nasal cavity with a decongestant solution, it is possible to reach and decongest the entire mucous membrane including the maxillary sinus ostial area and open up the osties. It is also possible to administer corticosteroides or antibiotics as a solution or suspension, antihistamines or mucolytic agents and to irrigate the nasal mucous membrane. In addition it is possible to administer a solution containing a short-living isotop onto the nasal mucous membrane with the method and device according to the invention in order to study the nasal adsorption and/or absorption of different drugs. A further use is to administer drugs systemically via absorption through the nasal mucosa. Examples of drugs, which can be administered in this way are insulin, metoclopramide, hormones and peptides.

I claim:

1. A method for the administration of drugs in solutions into one nasal cavity comprising the steps of:
   bending the patient's head forward between 55°–90° from an upright position so that the opening between the nasal cavity and the pharynx is positioned higher than the opening between the two nasal cavities; and
   introducing a drug-containing solution into one nostril, while the other nostril remains open to the air, in an amount to substantially fill the one nasal cavity and in a manner to allow any excess solution to flow into and drain freely from the other nasal cavity so as to avoid flowing down the pharynx.

2. A method according to claim 1, wherein the patient's head is bent forward at an angle of about 60°.

3. A method according to claim 1, wherein the patient's head is bent forward at an angle of about 90° so that solution covers the osties of the rear ethmoidal cells and sphenoidal sinus.

4. A method according to claim 1, wherein the solution is administered through a device having an upper opening part that tightly fits a human nostril, and comprising the step of maintaining solution in the nasal cavity for a selected period of time.

5. A method according to claim 4, comprising the step of alternatively withdrawing and reintroducing solution through said upper opening part, so as to keep the solution in said nasal cavity in motion.

6. A method according to claim 4, wherein solution is introduced through said upper opening part without spraying.

7. A method according to claim 6, comprising the steps of storing the solution in a compressible container and supplying the solution to said upper opening part by squeezing the container.

8. A method according to claim 6, comprising the steps of storing the solution in a rigid container and of controlling the supply of solution to said upper opening part by varying the height of the container.

* * * * *